US007677601B2

(12) United States Patent
Garett

(10) Patent No.: US 7,677,601 B2
(45) Date of Patent: Mar. 16, 2010

(54) PATIENT STARTER KITS

(76) Inventor: John Garett, 14 Murray Ave., Port Washington, NY (US) 11050

( * ) Notice: Subject to any disclaimer, the term of this patent is extended or adjusted under 35 U.S.C. 154(b) by 172 days.

(21) Appl. No.: 11/789,047

(22) Filed: Apr. 23, 2007

(65) Prior Publication Data

US 2008/0018095 A1 Jan. 24, 2008

Related U.S. Application Data

(60) Provisional application No. 60/809,767, filed on May 31, 2006.

(51) Int. Cl.

| | |
|---|---|
| ***B42D 15/00*** | (2006.01) |
| ***B65D 69/00*** | (2006.01) |
| ***B65D 71/00*** | (2006.01) |
| ***B65D 85/00*** | (2006.01) |
| ***A61B 17/06*** | (2006.01) |
| ***A61B 19/02*** | (2006.01) |
| ***A61L 15/00*** | (2006.01) |

(52) U.S. Cl. ......................... 283/67; 283/117; 283/900; 206/570; 206/425; 206/459.5; 206/438

(58) Field of Classification Search ................. 36/25 R, 36/27, 28, 59 C, 59 R, 103, 107; 206/238, 206/459.5, 528, 529, 534, 534.1, 534.2, 538, 206/543, 570, 571, 572; 211/181.1; 283/56, 283/72, 900; 383/106, 109; *A43B 13/14; A47F 5/14; B42D 15/00; B65D 33/04, 69/00*

See application file for complete search history.

(56) References Cited

U.S. PATENT DOCUMENTS

| | | | | |
|---|---|---|---|---|
| 5,191,975 | A * | 3/1993 | Pezzoli et al. | 206/151 |
| 5,931,304 | A * | 8/1999 | Hammond | 206/570 |
| 6,375,225 | B1 * | 4/2002 | Lapsker | 283/56 |
| 6,789,332 | B1 * | 9/2004 | Scholz | 36/27 |
| 7,007,615 | B2 * | 3/2006 | Grueneberg | 108/165 |
| 2004/0076347 | A1 * | 4/2004 | Johnson | 383/106 |
| 2004/0176987 | A1 * | 9/2004 | Dial et al. | 705/4 |
| 2004/0182810 | A1 * | 9/2004 | Rosen | 211/181.1 |

* cited by examiner

*Primary Examiner*—Dana Ross
*Assistant Examiner*—Justin V Lewis
(74) *Attorney, Agent, or Firm*—Katten Muchin Rosenman LLP

(57) ABSTRACT

A patient starter kit for distributing a product sample together with educational materials or additional product samples is disclosed. Integral to the kit is a one or a two-compartment packaging technique that provides pharmaceutical product samples in the same container as other patient drug information, disease state material and consumer product samples, coupons, other forms of media and/or related consumer products.

15 Claims, 6 Drawing Sheets

PATIENT STARTER KITS

CROSS-REFERENCE TO RELATED APPLICATION

This Application claims priority to U.S. Provisional No. 60/809,767 filed on May 31, 2006.

BACKGROUND OF THE INVENTION

The present invention relates to a device and method for packaging pharmaceutical product samples together with patient drug and disease state information, literature and other forms of media, and related consumer products, consumer package goods, devices, or services.

Prescription drug samples are widely employed by pharmaceutical firms, with the goal of increasing market share. Prescription drug samples have even recently been provided by pharmacy benefit managers and generic manufacturers.

However, the role of free drug samples is currently not to promote health literacy. Prescription drug samples are typically distributed to patients by physicians in their offices pursuant to a patient visit, often with little dialogue between the patient and physician regarding the medication. Currently, prescription samples or patient starter kits are neither informative for patients nor do they facilitate patient learning and adherence. In fact, most often prescription drug samples do not contain a patient package insert or patient drug information sheet. Additionally, the prescription drug sample usually results in patients bypassing the pharmacy and missing an opportunity to be counseled by a pharmacist regarding their medication.

Low adherence with prescribed treatments is ubiquitous and undermines treatment benefits. Studies have shown a variety of adherence interventions may be effective including oral and written material, programmed learning, involving patients more in their care through monitoring, reinforcement and rewards. Patient education helps to ensure that the patient properly understands instructions on how to take the pharmaceutical such that the medication works optimally. Innovative approaches for patients to follow prescriptions for medications and become educated on their disease states are needed.

Another limitation of the current distribution of prescription drug samples is that the sample itself often becomes separated from any labeling or patient education literature, e.g. package insert or brochure, that is provided by the physician. The literature is frequently lost or destroyed before the sample of the prescription drug is taken. Therefore, there is a need for an improved container for prescription drug samples and patient education literature to enhance compliance and long term therapy persistence.

Accordingly, there is a need to provide a patient starter kit that combines a prescription drug sample and patient/disease state resources which is designed to deliver pharmaceutical product instructions and information as well as disease state information to patients.

This is accomplished through a new packaging technique for a patient starter kit that makes it possible to provide pharmaceutical drug samples in the same container as other patient drug information, disease state material and consumer product samples or coupons.

SUMMARY OF THE INVENTION

The present invention provides a patient starter kit with either a one or two compartment container which holds a prescription drug sample or samples or debit card, voucher card, loyalty card, co-pay card on paper voucher "representative" of a prescription drug "drug sample" together with patient and disease state information, literature and other forms of media, and related consumer products, consumer package goods, devices and services.

The first compartment contains the prescription drug "drug sample" which is visible or available to the patient. The first compartment is provided with a "recess" such as, but not limited to, a slot, shelf, pocket, well or sleeve, for positioning the prescription "drug sample" therein. The prescription drug sample is held in the recess via one or more tabs or, alternatively, enclosed within a cavity formed in the first compartment with one or more die cut opening, window(s) or apertures for viewing the drug sample. When held in a recess in the first compartment, the sample is the same size as the recess so as to fit securely therein and be immediately visible. When held in a cavity within the first compartment, the prescription drug sample contained therein may be viewed through a direct opening, window(s) or aperture(s).

The second compartment is provided with a cavity which contains the patient and disease state information, literature and other forms of media, related consumer products, consumer package goods, devices, or services (samples, coupons, or literature).

It is also understood that the present invention may also be directed to a single compartment containing the drug sample or representation of the drug sample such as and an envelope as a second compartment containing the patient and disease state information, literature and other forms of media, related consumer products, consumer package goods, devices, or services (samples, coupons, or literature).

The body of the two component container may be a box, envelope, container, bag, or pouch comprised of cardboard, paperboard, cloth, PVC, vinyl, plastic or other suitable or similar material.

The present invention overcomes the foregoing disadvantages of the prior art and provides a patient starter kit where the prescription sample and the patient and disease state information, literature and other forms of media, and related products and services are retained together for distribution in a manner that permits the product sample to be visible and/or available to the patient.

The general object of the present invention is to eliminate unsatisfactory results flowing from the current practice in the distribution of prescription drug samples so as to facilitate patient learning and encourage compliance, and adherence to therapy, thereby optimizing patient benefit from prescription drug samples. It is a further object of this invention to provide a patient starter kit with a combination container for holding prescription drug samples and patient and disease state information, literature and other forms of media, and related products and services to improve both medication adherence and treatment outcomes for lifestyle benefits.

Other objects and advantages of the invention will become apparent with reference to the following description and the accompanying drawings.

a) Improve "healthy life styles" to better manage changes in healthcare by patient.

b) Encourage "Patient Retention"—stay in communication with patient for long term education of patient.

c) Combine or share benefits of prescription drug and consumer product working in concert together to improve lifestyle or health.

d) "Add-value" to patient education experience.

e) Initiate patient education in doctor's office early.

f) Increases compliance, persistence and patient retention.

g) Provides meaningful dialogue between patient and physician.

h) Focus attention on patient well-being.

i) Introduce patients to potentially new and relevant consumer products and goods to help cope with disease or health care condition.

j) Improve "positive" perception of pharmaceutical company by patient.

k) Defray costs of patient drug sampling—makes more efficient to reach patients.

l) Accelerates patient's filling of prescriptions at pharmacy and within several hours after doctor visit.

m) Encourages and enhances "physician" education to better healthcare techniques by extending exchange between Sales Representative and physician by spending more time together.

DESCRIPTION OF THE INVENTION

The container of the invention has a front and back panel and a pair of opposite side panels, the side panels being also attached to a top and bottom panel of a selected width disposed between each of the side panels and the front and back panel, thereby forming a box. Alternatively, the container of the invention may be a bag, pouch, or any combination of a box, bag, envelope, container or pouch. The container is divided into two compartments or a single compartment, and is particularly adapted to contain prescription drug samples in a first compartment and patient and disease state information, literature and other forms of media, and related products and services in the second compartment, thus forming a unitary container that may be distributed to a patient as a patient starter kit.

Figure 1:
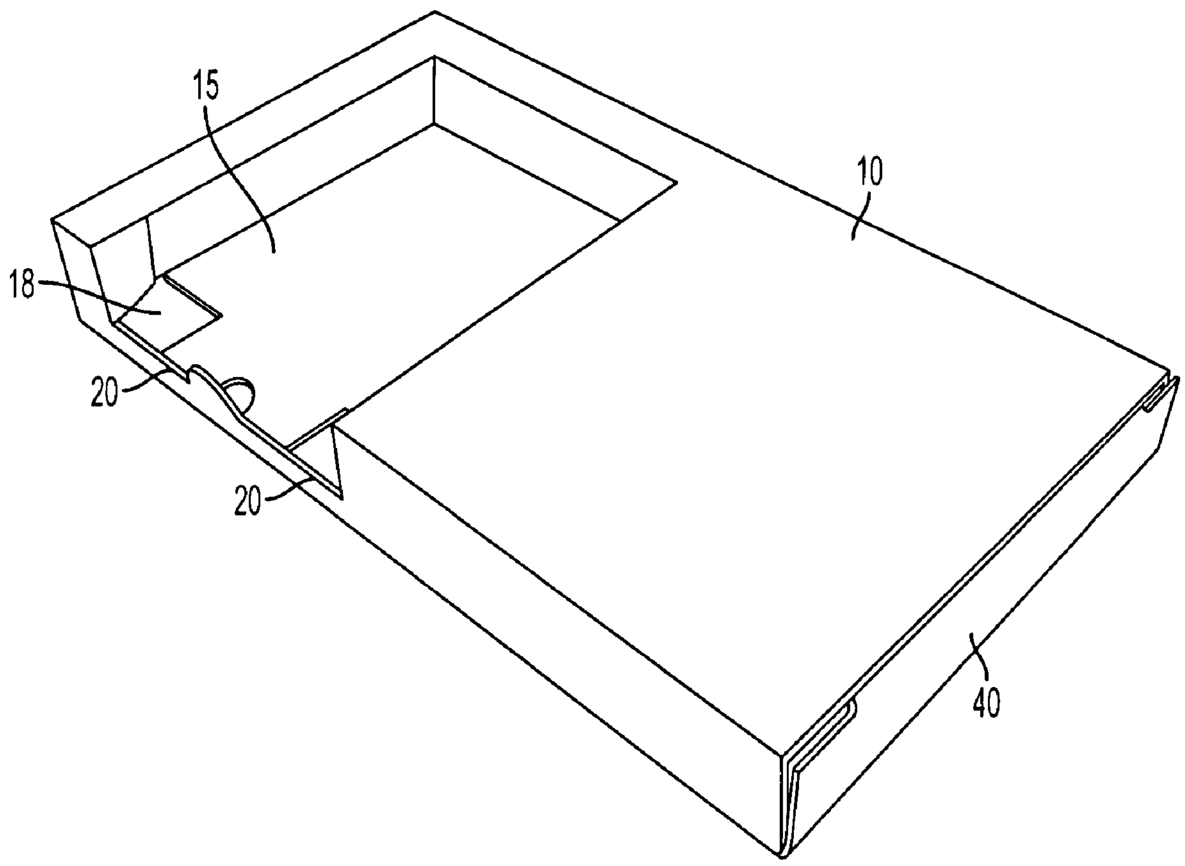
FIG. 1 is a perspective view of the container showing the recess and tab in the first compartment for holding the sample package.

Referring to FIG. 1, there is shown the preferred embodiment of the container 10 of the present invention, including the recess 15 and a tab 18 in the first compartment 20 for holding the prescription drug sample, debit card, voucher card, loyalty cord, co-pay card or paper voucher and a second compartment 40, for holding patient and disease state information, literature and other forms of media, and related products and services.

As shown in FIG. 1, the tab 18 is a cut out portion which functions as a securing means for retaining the sample package in position in the first component.

Figure 2:
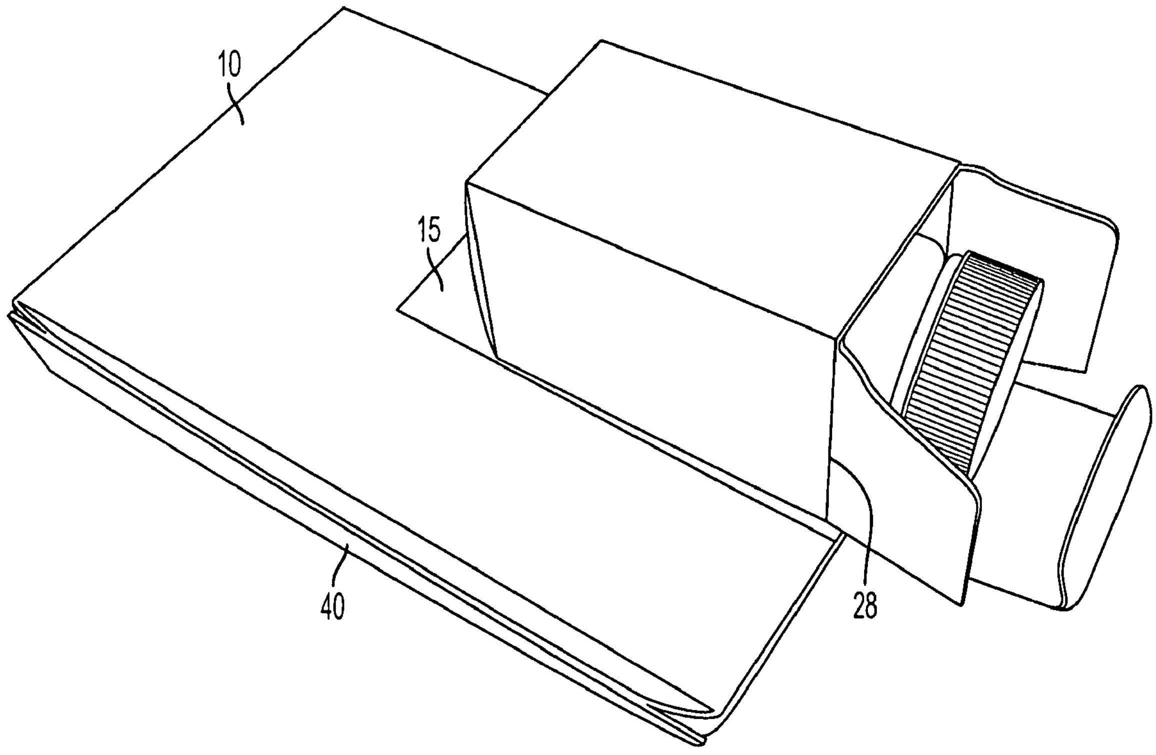
FIG. 2 is a right perspective view of the container showing the recess for holding the sample package and illustrating the sample package in position in the first compartment.

FIG. 2 is a right view exploded perspective illustrating the manner in which the prescription drug sample 28 and components which comprise the container are cooperatively arranged. Similarly, FIG. 3 is a left view exploded perspective illustrating the manner in which the components which comprise the container are cooperatively arranged.

Figure 3:
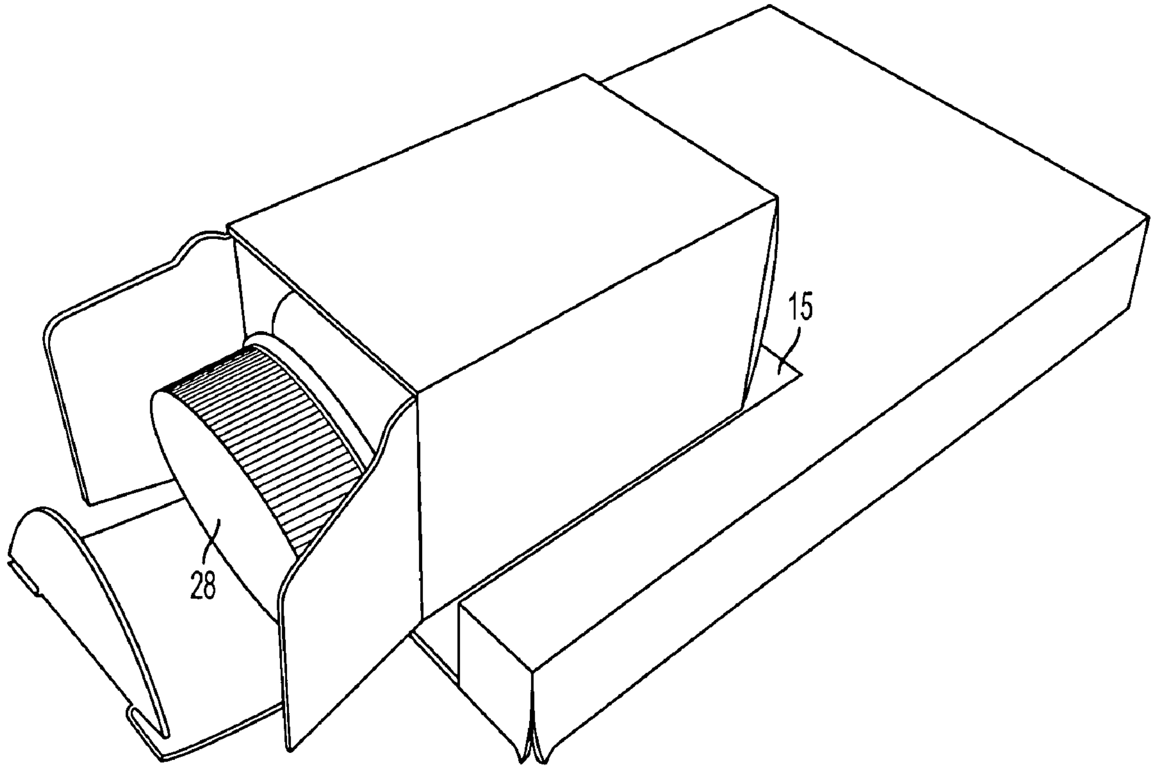
FIG. 3 is a left perspective view of the container showing the recess for holding the sample package and illustrating the sample package in position in the first compartment.

As show in FIGS. 2 and 3, the recess in the first compartment may be sloped downwardly from the side panel at an angle ranging from about 0° to about 70°. The angle facilitates the holding of the sample in place. The angle should be of sufficient depth to retain the sample package in position against accidental dislodgement. Alternatively, the combination of a tab and downwardly sloped recess in the first compartment may position the prescription drug sample to prevent accidental dislodgement.

Figure 4:
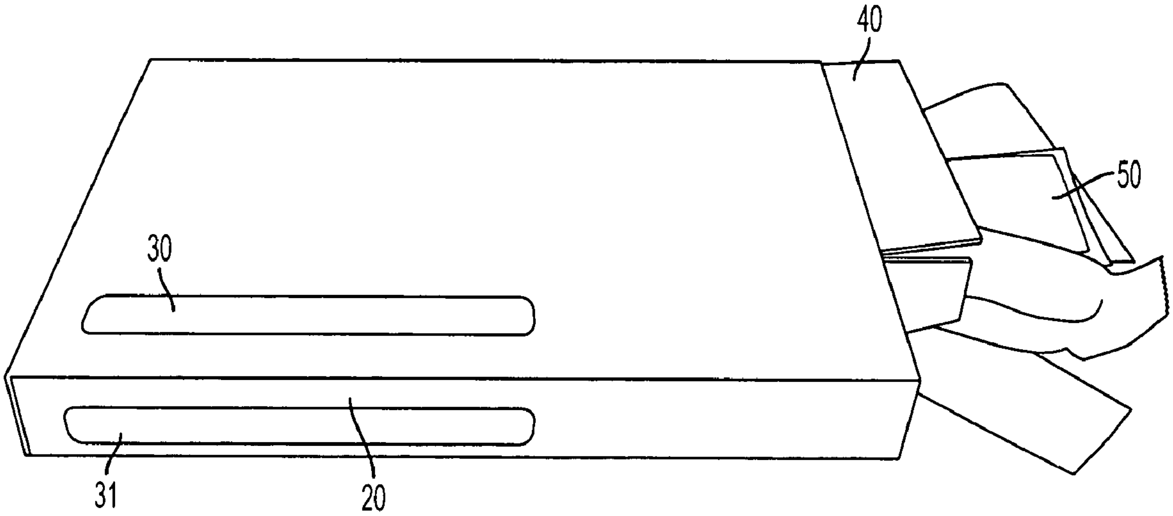
FIG. 4 is a perspective view of the container showing a window for viewing the sample and disclosing the contents of the second component.

FIG. 4 illustrates another embodiment of the invention, where the first compartment 20 encloses the prescription drug sample 28 and provides for window recesses or apertures 30, 31 and a second compartment 40, for holding patient and disease state information, literature and other forms of media, and related products and services 50.

As seen in FIG. 4, the aperture(s) or window recess(es) are located on the top and front panel of the container, so that the sample contained therein may be immediately visible. The apertures can be the same outline as the prescription drug sample so that the sample package is framed by the aperture. However, the aperture need not conform to the outline of the package but, the package must be visible from the aperture.

Figure 5:
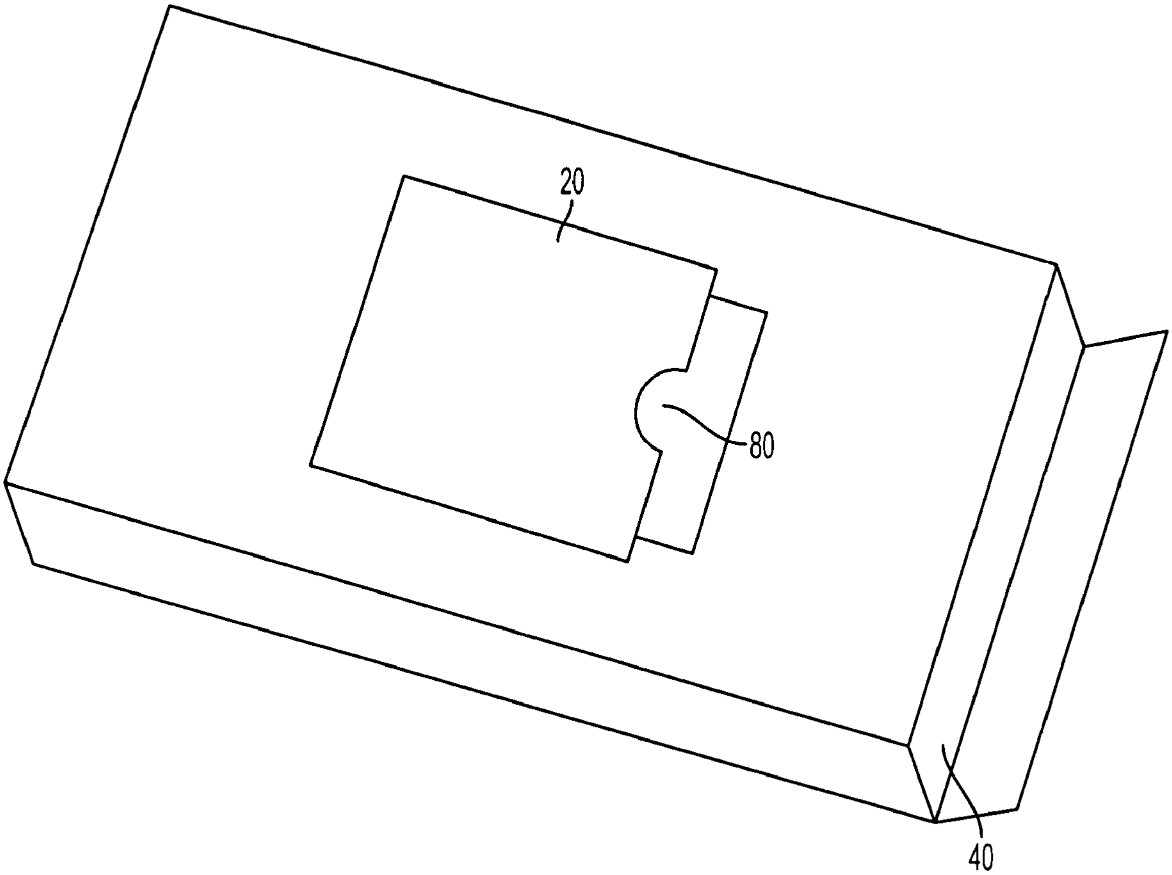
FIG. 5 is a right perspective view of the container showing a recess for holding the debit card, voucher card, loyalty card, co-pay card on paper voucher "representative" of a prescription drug "drug sample" together with a second compartment for patient and disease state information, literature and other forms of media, and related consumer products, consumer package goods, devices and services.

FIG. 5 shows, including the pocket 80 in the first compartment 20 for holding the prescription drug sample, or "representation" such as, but not including a debit card, voucher card, loyalty cord, co-pay card or paper voucher and a second compartment 40, for holding patient and disease state information, literature and other forms of media, and related products and services.

Figure 6:
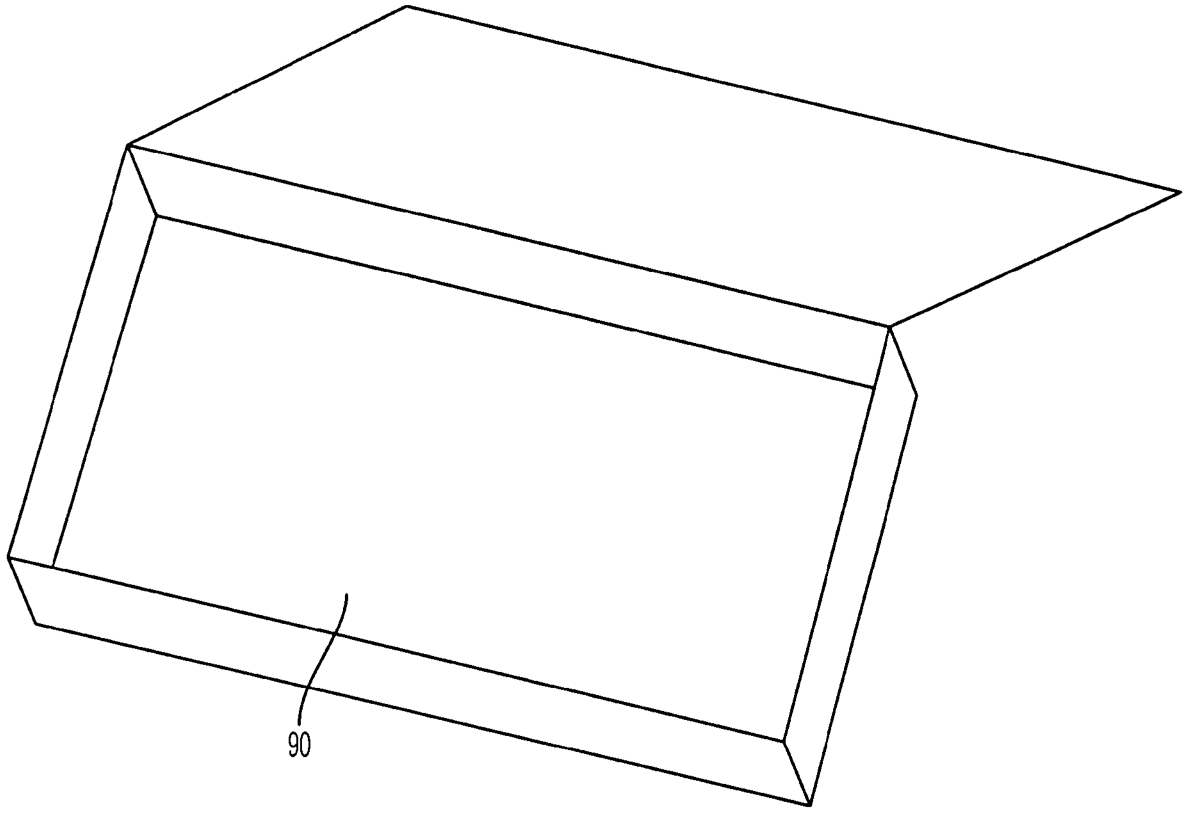
FIG. 6 is a right perspective view of a single compartment container containing both the drug sample or representation of the drug sample such as and an envelope as a second compartment containing the patient and disease state information, literature and other forms of media, related consumer products, consumer package goods, devices, or services (samples, coupons, or literature).

FIG. 6 shows a single container embodiment of the present invention containing both the drug sample or "representation" of the drug sample 28 (not shown) and an envelope 90 (not shown) as a second compartment containing the patient and disease state information, literature and other forms of media, related consumer products, consumer package goods, devices, or services (samples, coupons, or literature).

Prescription drug as defined herein includes both branded and generic pharmaceuticals that are not sold over-the-counter (OTC). It is understood that OTC pharmaceuticals as defined under the Food Drug & Cosmetic Act and including but not limited to aspirin, laxatives, antacids, cough cold products may be contained within the second compartment. The second compartment may also include medical devices therein. Such devices include, but are not limited to, glucose test strips, lancets, band aids, glucometers, pedometers, pulsox readers, nebulizers, and the like.

The term "prescription drug sample" is as defined under The Prescription Drug Marketing Act (PDMA) (Public Law 100-293) enacted on Apr. 22, 1988, and modified by the PDA (Public Law 102-353, 106 Stat. 941) on Aug. 26, 1992.

As used herein the phrase "patient adherence" is synonymous with the phrase "patient concordance" which refers to the process whereby the patient and physician reach an agreement on how a drug will be used, if at all and the phrase "patient compliance" or "patient compliance and persistence". Patient retention is defined as communication with the patient.

The phrase "prescription drug information" refers to information regarding the identification, uses, dosage, precautions, side effects, storage information, drug interaction information of the pharmaceutical sample provided. Such information may be provided in printed, electronic or other media format including, but not limited to, patient brochures, patient package inserts, web site information, CDs, DVDs, tapes, or memory sticks.

The phrase "disease state information" as used herein refers to an awareness of a particular condition and outcomes of treatment and their characteristics, including benefits and possible harms.

Suitable disease states include both acute, chronic conditions and lifestyle decisions (e.g. hair restoration, erectile dysfunction, dermatological, contraception) for which a prescription drug may be prescribed. Examples of suitable disease states for the patient starter kits of the present invention include, but are not limited to, arthritis (e.g. osteoarthritis, rheumatoid arthritis), hyperlipidemia, asthma, allergies, respiratory illnesses, osteoporosis, contraception, erectile dysfunction, hair restoration, overactive bladder, diabetes, obesity, hypertension, congestive heart failure, peripheral arterial disease, stroke, insomnia, migraine, infections, GI disorders, and acid reflux with all above conditions affecting adults and children.

The phrase "consumer package goods" as used herein refers to food, retail beverage and dairy products, condiments, smoking cessation products, ethnic products, health and beauty aids, OTC products, health, beauty and cosmetic products, weight control products, fitness shoes, exercise apparel, and the like.

The phrase "related consumer products" as used herein refers to, but is not limited to, coupons, product samples, medical devices, and medical services.

The phrase "consumer services" as used herein refers to, but is not limited to, clubs, retail associations, memberships (e.g. gym or spa), pharmacy services, pharmacies, financial security services, health insurance or HMO/PPO services.

The first component may be sized and configured to receive a variety of sizes of prescription drug sample packages or only patient education literature. The aperture or window of the first compartment can be sized and configured to permit viewing of the prescription drug sample (or voucher, debit card, discount card) therein as appropriate. Alternatively, when the container is a bag, the first component may be a single compartment, such as a zippered compartment or a pouch or pocket.

Alternatively, the first compartment may contain either in lieu of, or together with, the prescription drug sample, a means for obtaining the prescription drug. The means for obtaining a prescription drug include, but are not limited to, a prescription, a reimbursement for the cost of the first prescription such as a prescription voucher, a prescription discount card, enrollment information for a prescription discount program, a prescription co-pay waiver, a prescription co-pay discount, a coupon for a trial sample and combinations thereof. Prescription discount cards offer patient lower drug prices by reducing pharmacy dispensing fees, using less costly outlets such as the Internet and mail order, and negotiating discounts from pharmacies and drug manufacturers.

The contents of the second compartment are concealed from view. However, in an alternative embodiment, the container may be made from transparent material in which case the contents of the second compartment are immediately visible. Alternatively, when the container is a bag, the second component may be a compartment, such as a zippered compartment or a pouch or pocket.

The sample may be held in position via tabs. Alternatively, the sample may be adhesively secured in the recess via glue or thermoplastic material, or may be secured via any other means such as VELCRO®. Alternatively, the first compartment may contain samples of more than one prescription drug, such as from two classes of drugs employed in the therapeutic regimen of a particular disease state or lifestyle decision. For example, an oral anti-hypertensive sample and a diuretic sample, or a beta-blocker sample and an ACE inhibitor sample may be provided in the first component. Nothing herein is meant to limit the contents of first compartment to a single pharmaceutical drug sample.

In another embodiment, one or more patient starter kits are positioned in a tray-organizer that holds the individual patient kits for display or storage in the sample storage area. This tray may possess two or more tabs or short protruding leg extensions at the front bottom of the tray which hangs slightly over the edge of the storage shelf. The tabs cling or grip the shelf edge to prevent the tray from sliding or being pushed back on the shelf.

Nothing herein is meant to limit the size or shape of the container. Variations in the form, proportion, size and minor details of the structure of the container may be made without departing from the spirit or sacrificing any of the advantages of the invention. The container should be readily openable, economical to produce, and lend itself to pre-printing and mass production techniques. It is understood that the container itself can be printed with advertising, "brand" identification, descriptive or identifying data relating to the contents. Further, the container of the patient starter kit of the present invention may contain a plurality of compartments for holding the patient drug and disease state information, literature and other forms of media, and related products and services.

It has been well established that that the use of patient education can improve patient knowledge of disease processes, improve clinical outcomes, and enhance overall patient satisfaction. With an increasing number of patients and the economic reality of limited physician time per patient, the physician-patient encounter often leaves patients feeling uneducated about both their disease state and medication.

The present invention provides prescription samples and educational materials, and consumer goods, products and services at the point-of-care. The patient starter kits of the present invention enhance patient compliance, adherence to therapy, and patient retention. The kits may be received by the patients from the physician at the "moment of diagnosis", thereby enhancing the patient's "point of care" experience in the physician office.

In one embodiment, the first compartment contains an oral anti-diabetic agent, and the second compartment contains patient and disease state information, literature and other forms of media, and related products and services pertaining to the regimen for type 2 diabetes mellitus. More specifically, the second compartment includes information, literature and other forms of media, and related products and services pertaining to diet such as meal planning and carbohydrate counting, increased exercise, smoking cessation, oral hypoglycemic drugs, and risk factor management, for example, footcare and wound care, in the forms of consumer coupons and product samples.

In a second embodiment, the first compartment contains an oral anti-lipidemic drug, and the second compartment contains information, literature and other forms of media, and related products and services pertaining to diet such as low cholesterol meals, and increased dietary fiber, and cholesterol checking devices, in the form of consumer coupons or product samples.

In yet another embodiment, the first compartment contains a cardiovascular drug, and the second compartment contains education programs, self management action plans, symptom monitoring device coupons and related OTC products, in the form of consumer coupons or product samples.

In yet another embodiment, the first compartment contains a means of obtaining a prescription drug such as a coupon for a trial sample, and the second compartment contains patient education literature and coupons.

In yet another embodiment, the patient starter kit contains more than two compartments where the first compartment contains the prescription drug sample or means to obtain the sample, the second or more compartments contains the patient and disease state information, literature and other forms of media, related consumer products, consumer package goods, devices, or services (samples, coupons, or literature).

EXAMPLE 1

A patient starter kit where the first compartment contains an oral hypoglycemic agent such as metformin, rosglitazone, piloglitazone, glipizide, and the second compartment contains diabetic footcare educational material such as a footcare guide, instructional CD or DVD, a tube of moisturizer, a coupon for odor control foot spray, together with a pair of insoles, a nail file, and a hand mirror.

EXAMPLE 2

A patient starter kit where the first compartment contains an oral anti-lipidemic drug such as simvastatin, lovastatin, fenofibrate, gemfibrozil, and the second compartment contains literature pertaining to the specific pharmaceutical in the first compartment, adjunctive disease state literature for maintaining a heart healthy low-cholesterol diet, coupons for egg or butter substitutes, high grain cereals, or gym memberships, and samples of salt substitutes, aspirin 81 mg enteric coated tablets, Vitamin E or Omega 3 fatty acid capsules, smoking cessation rebate and running shoe coupons.

EXAMPLE 3

A patient starter kit where the first compartment contains a prescription antibiotic such as azithromycin, ciprofloxacin, erythromycin, levofloxacin, amoxacillin, and the second compartment contains an OTC antipyretic such as acetaminophen, aspirin or ibuprofen, and coupons for cough/cold products, tissues, atomizers, and humidifiers.

While this invention has been described, it will be understood that it is capable of further modification, uses and/or adaptations of the invention following in general the principal of the invention and including such departures from the present disclosure as come within known or customary practice in the art to which the invention pertains, and as may be applied to the essential features hereinbefore set forth, as fall within the scope of the invention or the limits of the appended claims.

What is claimed is:

1. A patient starter kit comprising a body having a front and back panel and a pair of opposite side panels, the side panels being attached to a top and bottom panel of a selected width disposed between each of the side panels and the front and back panel, and the patient starter kit having at least two compartments, a first compartment defining a first recess formed into the front panel for positioning a pharmaceutical product sample or sample representation and a second or more compartments provided with a second cavity for items selected from the group consisting of patient drug information, disease state information, literature, other forms of media, related consumer products, coupons, product samples or consumer literature, and medical devices, wherein the first recess is configured such that the pharmaceutical product sample or sample representation fits securely in the first recess, and wherein said pharmaceutical product sample or sample representation is available or visible to the patient.

2. The patient starter kit of claim 1, wherein said sample representation is selected from the group consisting of a debit card, a voucher card, a loyalty card and a copay card.

3. The patient starter kit of claim 2, wherein the top panel comprises a tab that at least partially encloses the first recess for securing the sample package in position.

4. The patient starter kit of claim 1, wherein said first cavity comprises one or more windows for viewing or accessibility.

5. A patient starter kit having a body selected from the group consisting of a bag and pouch, and having a first compartment defining a first recess formed into the front panel for positioning a pharmaceutical product sample and a second compartment provided with a second cavity for items selected from the group consisting of patient drug information, disease state information, literature, other forms of media, and related consumer products, wherein the first recess is configured such that the pharmaceutical product sample or sample representation fits securely in the first recess, and wherein said pharmaceutical sample is visible or accessible to the patient.

6. The patient starter kit of claim 1, wherein said body comprises a material selected from the group consisting of cardboard, paperboard, cloth, vinyl, PVC, and plastic.

7. A patient starter kit having a body selected from the group consisting of a box, pouch or bag and having a first compartment defining a first recess formed into the front panel for positioning a means to obtain a pharmaceutical product sample and a second compartment provided with a second cavity for items selected from the group consisting of patient drug information, disease state information, literature, other forms of media, and related consumer products, wherein the first recess is configured such that the pharmaceutical product sample or sample representation fits securely in the first recess, and wherein said pharmaceutical sample is visible or accessible to the patient.

8. The patient starter kit of claim 7, wherein said means for obtaining a pharmaceutical product sample is selected from the group consisting of a prescription, a prescription discount card, a reimbursement for the cost of the first prescription, enrollment information for a prescription discount program, a prescription co-pay waiver, a prescription co-pay discount, a coupon for a trial sample, a coupon for refills, and combinations thereof.

9. A patient starter kit having a body selected from the group consisting of a box, a pouch, and a bag and having a first compartment defining a first recess formed into the front panel for positioning a drug sample or representation of the drug sample and a second compartment comprising an envelope, wherein the second compartment is contained within the first compartment and contains items selected from the group consisting of patient and disease state information, literature, other forms of media, related consumer products, consumer package goods, devices, services, samples, and coupons and wherein the first recess is configured such that the pharmaceutical product sample or sample representation fits securely in the first recess.

10. A method for improving patient adherence to prescription drug therapy comprising providing a patient starter kit comprising a body having a front and back panel and a pair of opposite side panels, the side panels being attached to a top and bottom panel of a selected width disposed between each of the side panels and the front and back panel, and the patient starter kit having at least two compartments, a first compartment defining a first recess formed into the front panel for positioning a pharmaceutical product sample or sample representation and a second or more compartments provided with a second cavity for items selected from the group consisting of patient drug information, disease state information, literature, other forms of media, related consumer products, coupons, product samples or consumer literature, and medical devices, wherein the first recess is configured such that the pharmaceutical product sample or sample representation fits securely in the first recess, and wherein said pharmaceutical product sample or sample representation is available or visible to the patient.

11. A method for improving patient adherence to prescription drug therapy as in claim 10 further comprising:

improving ease of use of prescription drug;

encouraging compliance and persistence faster and easier; and creating a "positive" patient experience.

12. The patient starter kit as in claim 1 further comprising a tray-organizer which holds one or more patient starter kits for display or storage.

13. The patient starter kit as in claim 12, wherein the tray-organizer comprises two protruding tabs, the two protruding tabs being located at the base of said tray organizer and configured to hang slightly over the edge of a shelf and grip said shelf thereby preventing dislocation.

14. The patient starter kit of claim 1, wherein the body comprises paperboard.

15. The patient starter kit of claim 1, wherein the recess is sloped downwardly at an angle ranging from about 0° to about 70°.

* * * * *